United States Patent
Mk et al.

(10) Patent No.: US 11,701,457 B2
(45) Date of Patent: Jul. 18, 2023

(54) ULTRA LOW-LEAKAGE SILICONE-BASED HEATER THERMALLY COUPLED TO A HEAT TRANSFER BODY

(71) Applicant: HONEYWELL INTERNATIONAL INC., Morris Plains, NJ (US)

(72) Inventors: Senthilkumar Mk, Morris Plains, NJ (US); George Whyte, Morris Plains, NJ (US); John Stopforth, Morris Plains, NJ (US); Claudia Acosta, Morris Plains, NJ (US); Marco Barron, Morris Plains, NJ (US); Anton Jeysing, Morris Plains, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 422 days.

(21) Appl. No.: 16/765,323

(22) PCT Filed: Dec. 4, 2017

(86) PCT No.: PCT/US2017/064451
§ 371 (c)(1),
(2) Date: May 19, 2020

(87) PCT Pub. No.: WO2019/112548
PCT Pub. Date: Jun. 13, 2019

(65) Prior Publication Data
US 2020/0353143 A1    Nov. 12, 2020

(51) Int. Cl.
*A61M 1/16* (2006.01)
*A61M 1/28* (2006.01)

(52) U.S. Cl.
CPC ............ *A61M 1/1664* (2014.02); *A61M 1/28* (2013.01); *A61M 2205/0233* (2013.01);
(Continued)

(58) Field of Classification Search
None
See application file for complete search history.

(56) References Cited

U.S. PATENT DOCUMENTS

| | | | | |
|---|---|---|---|---|
| 5,381,510 | A | * | 1/1995 | Ford .................... H05B 3/36 165/169 |
| 6,125,695 | A | * | 10/2000 | Alvesteffer ............ G01F 1/698 73/204.27 |

(Continued)

FOREIGN PATENT DOCUMENTS

WO    2012/155149 A2    11/2012

OTHER PUBLICATIONS

International Search Report and Written Opinion received for PCT Patent Application No. PCT/US2017/064451, dated Aug. 27, 2018, 10 pages.

(Continued)

*Primary Examiner* — Jonathan M Peo
(74) *Attorney, Agent, or Firm* — Alston & Bird LLP

(57) ABSTRACT

Systems and methods include a heat transfer body with opposing major surfaces formed from a thermally conductive substrate in intimate thermal interaction with an alumina exterior surface that extends across the major surfaces of the body. In an illustrative example, the heat source may be a substantially planar, silicone-based heater source (P-SBHS). The heat transfer body may be configured to thermally interact, for example, heat from a heat source proximate a first of the major surfaces to a second of the major surfaces. A temperature sensor module may be located, for example, proximate to the first major surface such that a temperature sensor thermally interacts with the first major surface. The temperature sensor module may, for example, insulate the temperature sensor from the P-SBHS.

14 Claims, 8 Drawing Sheets

(52) U.S. Cl.
CPC ............... *A61M 2205/3368* (2013.01); *A61M 2205/3538* (2013.01); *A61M 2205/3633* (2013.01); *A61M 2205/3673* (2013.01)

(56) References Cited

U.S. PATENT DOCUMENTS

| | | | | |
|---|---|---|---|---|
| 6,142,974 | A | * | 11/2000 | Kistner ................. F28D 7/0066 604/113 |
| 2006/0065276 | A1 | | 3/2006 | Kammer et al. |
| 2014/0072288 | A1 | | 3/2014 | Newell |
| 2014/0199057 | A1 | * | 7/2014 | Hansen ............... A61M 1/1664 392/443 |
| 2016/0074599 | A1 | | 3/2016 | Faries, Jr. et al. |
| 2018/0216846 | A1 | | 8/2018 | Newell |
| 2018/0236180 | A1 | * | 8/2018 | Andersen ............. H05B 1/0244 |

OTHER PUBLICATIONS

International Search Report of the International Searching Authority for PCT/US2017/064451 dated Aug. 27, 2018.

* cited by examiner

ULTRA LOW-LEAKAGE SILICONE-BASED HEATER THERMALLY COUPLED TO A HEAT TRANSFER BODY

TECHNICAL FIELD

Various embodiments relate generally to heaters on medical devices.

BACKGROUND

Kidneys provide waste product filtering from an individual's blood supply. Systemically the kidneys may help regulate blood pressure, provide electrolyte balance, and may be involved with producing red blood cells. Some people may experience progressive kidney failure, and may be provided treatment for its underlying causes. For some individuals, various stages of kidney failure may necessitate regular dialysis treatments.

Dialysis treatments may cleanse the body of various waste products. A dialysis machine may provide this treatment by use of a filter system. In one type of dialysis, peritoneal dialysis, a catheter is surgically placed through a patient's abdominal wall. A dialysate is then administered into the patient's peritoneal cavity via the catheter. The dialysate may remain in the patient for a few hours, then be drained out. This process may leech various waste products from the blood, and may aid in replacing normal kidney function. Before the dialysate is administered into the patient, it may be warmed to body temperature. Warming the dialysate may mitigate patient discomfort.

Hemodialysis is one type of renal replacement therapy that filters waste, removes extra fluid, and balances electrolytes. In hemodialysis, blood may be removed from the body and filtered through a man-made membrane called a dialyzer, or artificial kidney. The filtered blood may then be returned to the body. There may be different access types for hemodialysis (e.g., arteriovenous (AV) fistula, AV graft, and central venous catheter).

Intravenous therapy is therapy that delivers liquid substances directly into a vein. The intravenous (IV) route of administration can be used for injections or infusions. The intravenous route may be the fastest way to deliver medications and fluid replacement throughout the body, because the body's circulatory system carries them. Intravenous therapy may be used for fluid replacement, to correct electrolyte imbalances, to deliver medications, and for blood transfusions.

SUMMARY

Systems and methods include a heat transfer body with opposing major surfaces formed from a thermally conductive substrate in intimate thermal interaction with an alumina exterior surface that extends across the major surfaces of the body. In an illustrative example, the heat source may be a substantially planar, silicone-based heater source (P-SBHS). The heat transfer body may be configured to thermally interact, for example, heat from a heat source proximate a first of the major surfaces to a second of the major surfaces. A temperature sensor module may be located, for example, proximate to the first major surface such that a temperature sensor thermally interacts with the first major surface. The temperature sensor module may, for example, insulate the temperature sensor from the P-SBHS. The electrical insulation provided by the alumina exterior surface may reduce electrical leakage currents induced between the P-SBHS and, for example, patient and/or operator accessible parts.

Various embodiments may achieve one or more advantages. For example, some implementations may accurately measure the temperature of the warming tray and may advantageously provide more accurate control of the temperature of various fluids being warmed. In some examples, labor involved with assembly of the warming tray may be reduced. Various embodiments may accommodate non-planar warming trays which may advantageously provide an effective retention mechanism for the fluid bags being warmed.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 3:
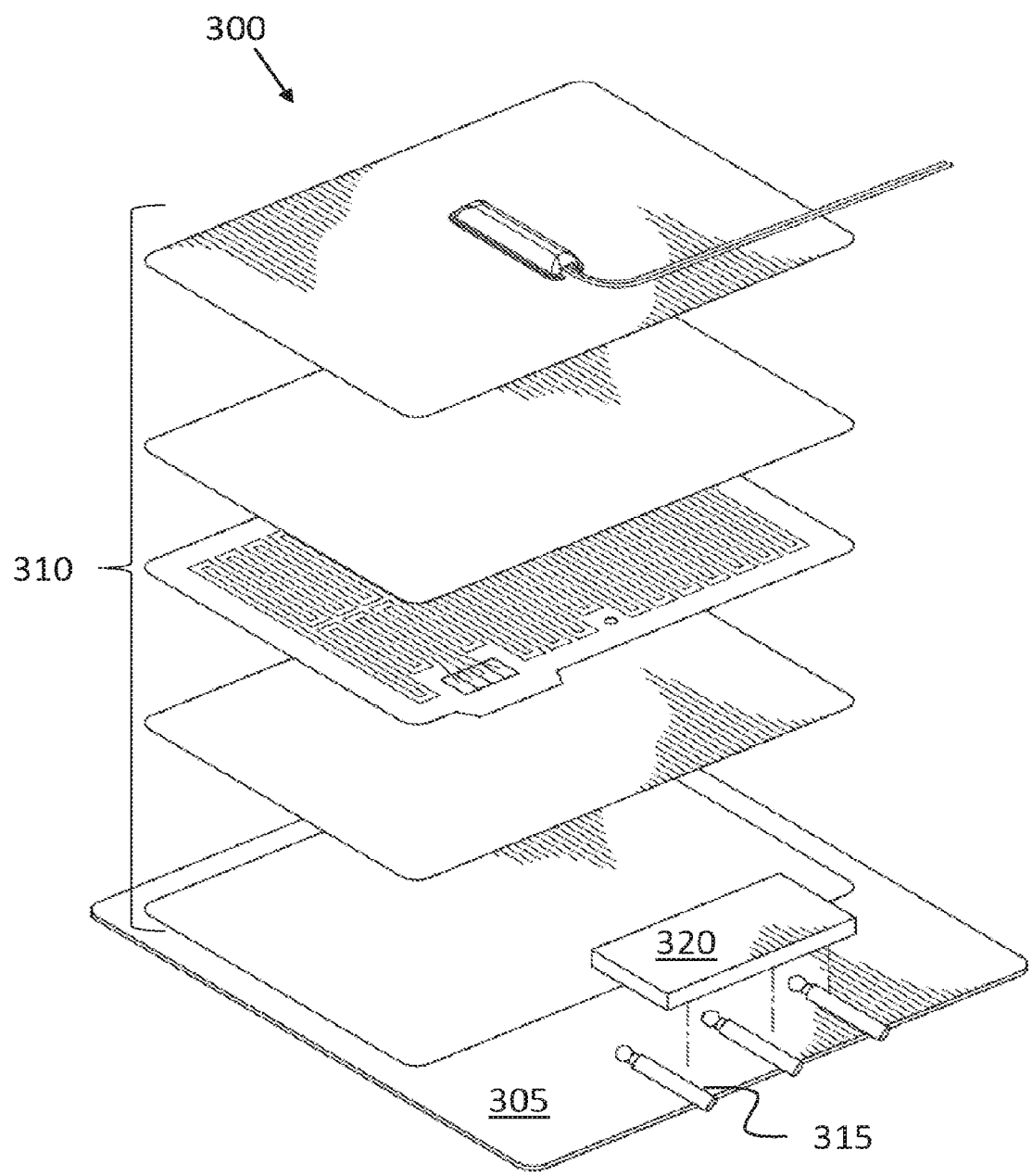
FIG. 3 depicts an exploded view of an exemplary heat source with exemplary temperature modules placed outside the perimeter of the heat source.
Figure 4:
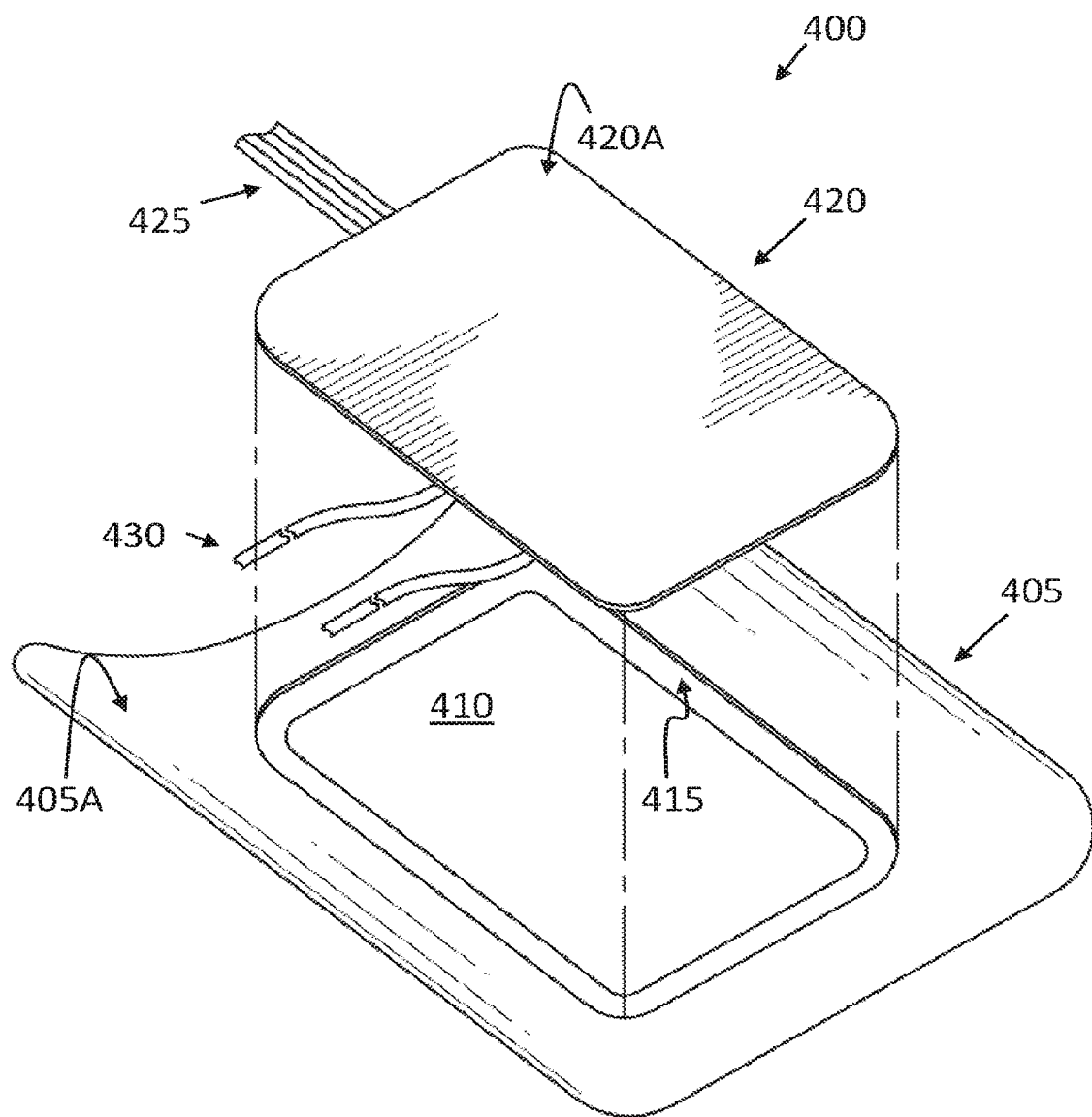
FIG. 4 depicts an exploded perspective view of an exemplary heater tray in a drop-in form factor.
Figure 5:
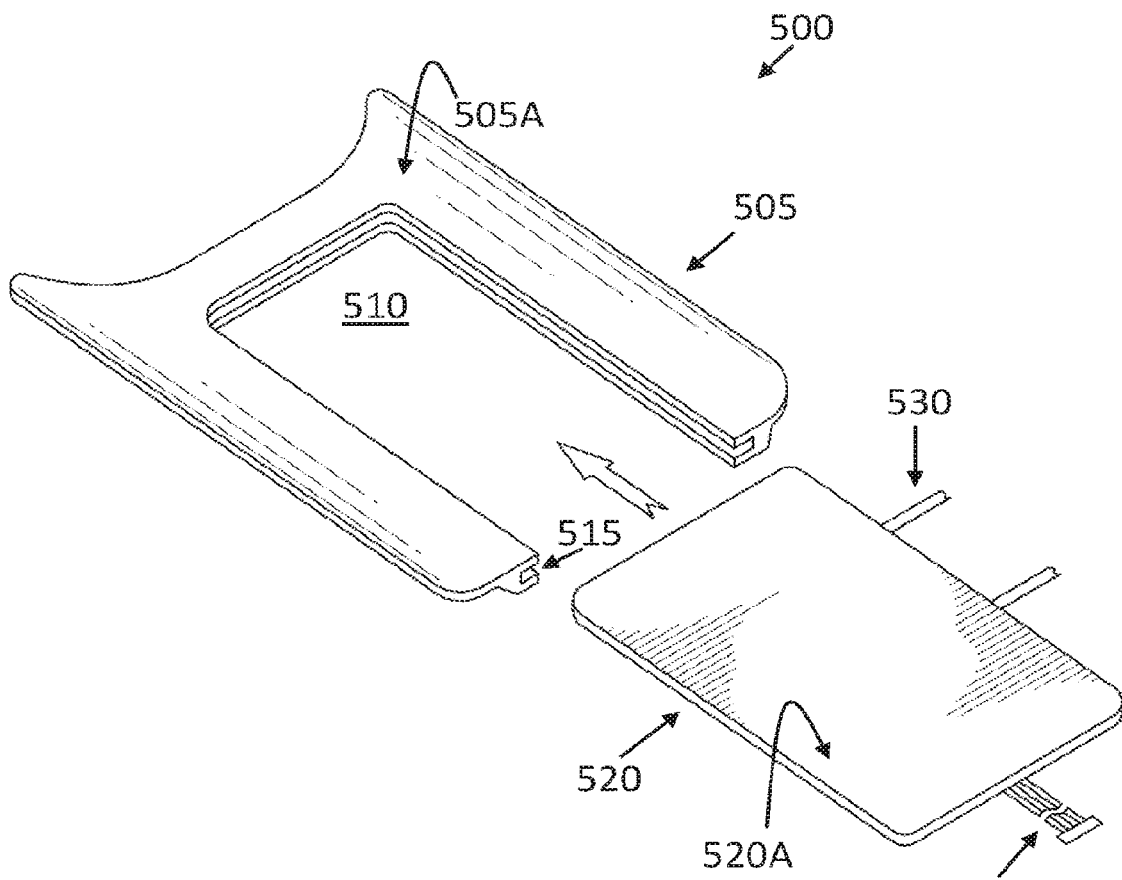
FIG. 5 depicts an exploded perspective view of an exemplary heater tray in a slide-in form factor.

To aid understanding, this document is organized as follows. First, a chemically formed layer of alumina on a heater subassembly is briefly introduced with reference to FIGS. 1A and 1B. Second, with reference to FIGS. 2A, 2B and 2C the discussion turns to various views of an exemplary embodiment illustrating a temperature monitoring sub-module mounted on a heater subassembly. In FIG. 3, an additional exemplary temperature monitoring embodiment is discussed. Finally, FIGS. 4 and 5 present exemplary embodiments illustrating mounting methods of the heater subassembly.

Figure 1A:
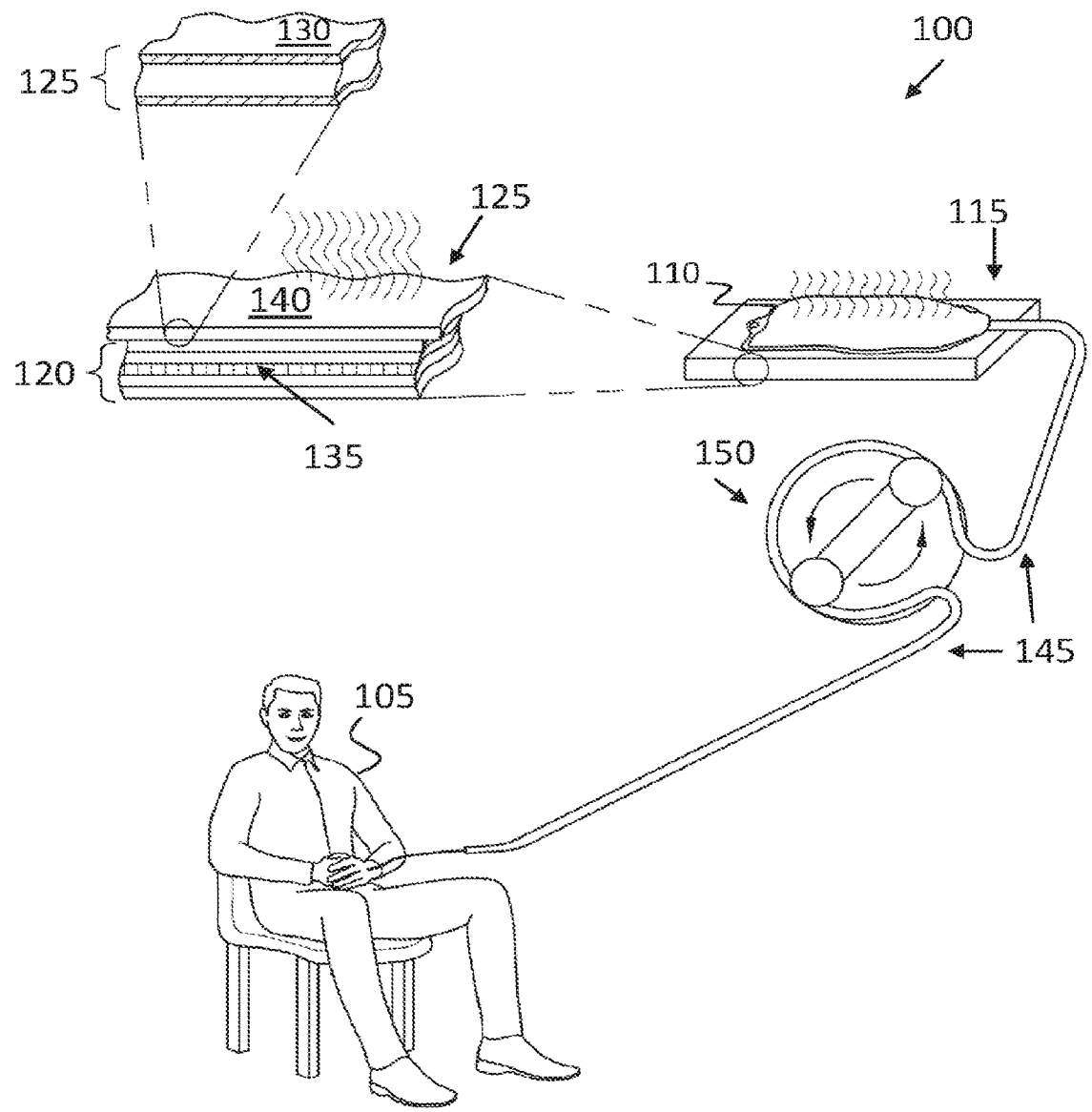
FIG. 1A depicts an intravenous process where a blood product administered to a patient is warmed by an exemplary warming tray including a warming substrate with a chemically formed layer of alumina.

FIG. 1A depicts an intravenous process where a blood product administered to a patient is warmed by an exemplary warming tray including a warming substrate with a chemically formed layer of alumina. An intravenous treatment example 100 includes a patient 105. The patient 105 is receiving a blood product 110. The blood product 110 is heated by a warming tray assembly 115. The warming tray assembly 115 includes a heat source 120. The heat source 120 is thermally coupled to a heat transfer body 125. The heat transfer body 125 includes a chemically formed layer of alumina 130.

The chemically formed layer of alumina 130 may mitigate electrical leakage currents from active electrical circuits 135 within the heat source 120. The chemically formed layer of alumina 130 may provide substantial electrical insulation between the active electrical circuits 135 and external operator/patient accessible surfaces 140. The term "substantial electrical insulation" in this case may refer to insulation that limits electrical leakage current to a predetermined criteria for example, less than about 0.1 µA, 0.2 µA, 0.25 µA, 0.3 µA, 0.4 µA, 0.5 µA, 0.6 µA, 0.7 µA, 0.75 µA, 0.8 µA, 0.9 µA, 1 µA, 2 µA, 3 µA, 4 µA, 5 µA, 6 µA, 7 µA, 8 µA, 9 µA, 10 µA, 20 µA, 25 µA, 30 µA, 40 µA, or up to at least about 50 µA.

The blood product 110 is administered to the patient 105 through a tubing set 145. The tubing set 145 is applied to a pump 150. The pump 150 is operable to move the warmed blood product 110 to the patient 105. In some examples, the warming tray assembly 115 may be part of a system administering dialysis or other forms of treatment administered directly into bloodstream. These systems may administer fluids, medications, or blood products. Various systems including the warming tray assembly 115 may remove body toxins or excess fluids.

Figure 1B:
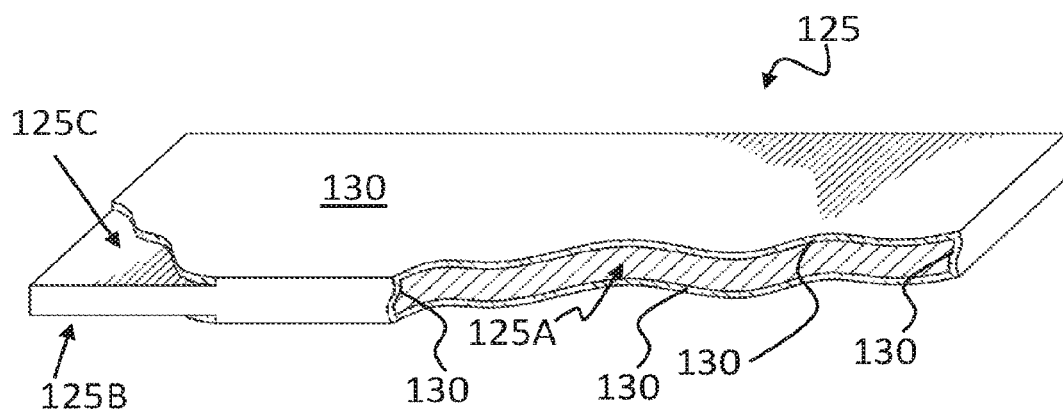
FIG. 1B depicts a perspective cut-away view of an exemplary heat transfer body made up of a conductive substrate with a chemically formed layer of alumina for mitigation of electrical leakage current.

FIG. 1B depicts a perspective cut-away view of an exemplary heat transfer body made up of a thermally conductive substrate with a chemically formed layer of alumina for mitigation of electrical leakage current. In the depicted example, the heat transfer body 125 includes a thermally conductive substrate 125A. The thermally conductive substrate 125A includes a major surface 125B on the bottom of the thermally conductive substrate 125A and an opposing major surface 125C on the top of the thermally conductive substrate 125A. The thermally conductive substrate 125A is covered on all sides by the chemically formed layer of alumina 130. In some examples, the chemically formed layer of alumina 130 may be an exterior surface. In some examples, the warming substrate 125 may be formed, in whole or in part, of aluminum. Some examples of warming substrates 125 may be formed of various aluminum alloys.

Figure 2A:
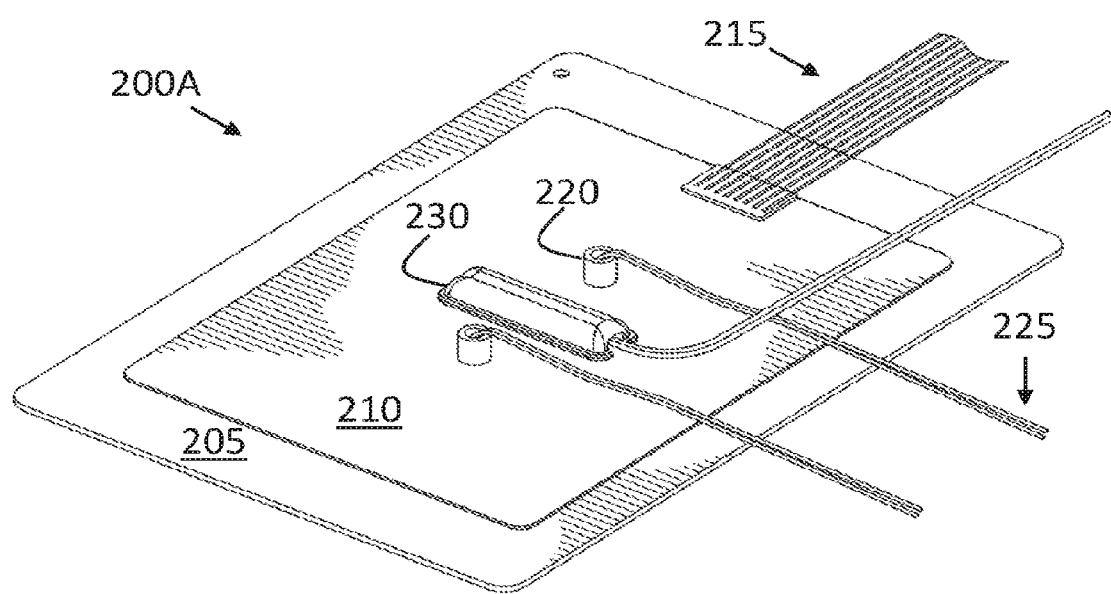
FIG. 2A depicts an exemplary heat source and exemplary temperature modules thermally coupled to a heat transfer body.

FIG. 2A depicts an exemplary heat source and exemplary temperature modules thermally coupled to a heat transfer body. A heating surface subassembly 200A includes a heat transfer body 205. The heat transfer body 205 is thermally coupled to a heat source 210. The heat source 210 is electrically connected to an input power harness 215. In operation, the heat source 210 receives power from the input power harness 215 causing the heat source 210 to heat up. The heat source 210 includes an aperture for insertion of an insulating barrel 220. The barrel 220 may be inserted through the heat source 210 until it is in contact with the heat transfer body 205. Within the insulating barrel 220 is a temperature sensor assembly 225. The temperature sensor assembly 225 may sense and/or measure the temperature of the heat transfer body 205, yet may be thermally insulated from the proximate heating effects of the heat source by the insulating barrel 220. In some implementations, the insulating barrel 220 may include a non-thermally conductive ceramic. In various implementations, the insulating barrel 220 may include a non-thermally conductive plastic.

In the depicted example, a thermal breaker 230 is thermally coupled to the heat source 210. In operation, if the temperature of the heat source 210 exceeds a predetermined threshold for a predetermined amount of time, the thermal breaker 230 may electrically open. In some examples, the thermal breaker 230 may be connected in series with the input power harness 215 shutting off power to the heat source 210 when the heat source 210 exceeds a predetermined threshold for a predetermined time. In some embodiments, a control circuit (not shown) may receive a signal from the thermal breaker 230 in response to the heat source 210 exceeding a predetermined threshold for a predetermined time. Accordingly, the control circuit may turn off power to the heat source 210.

Figure 2B:
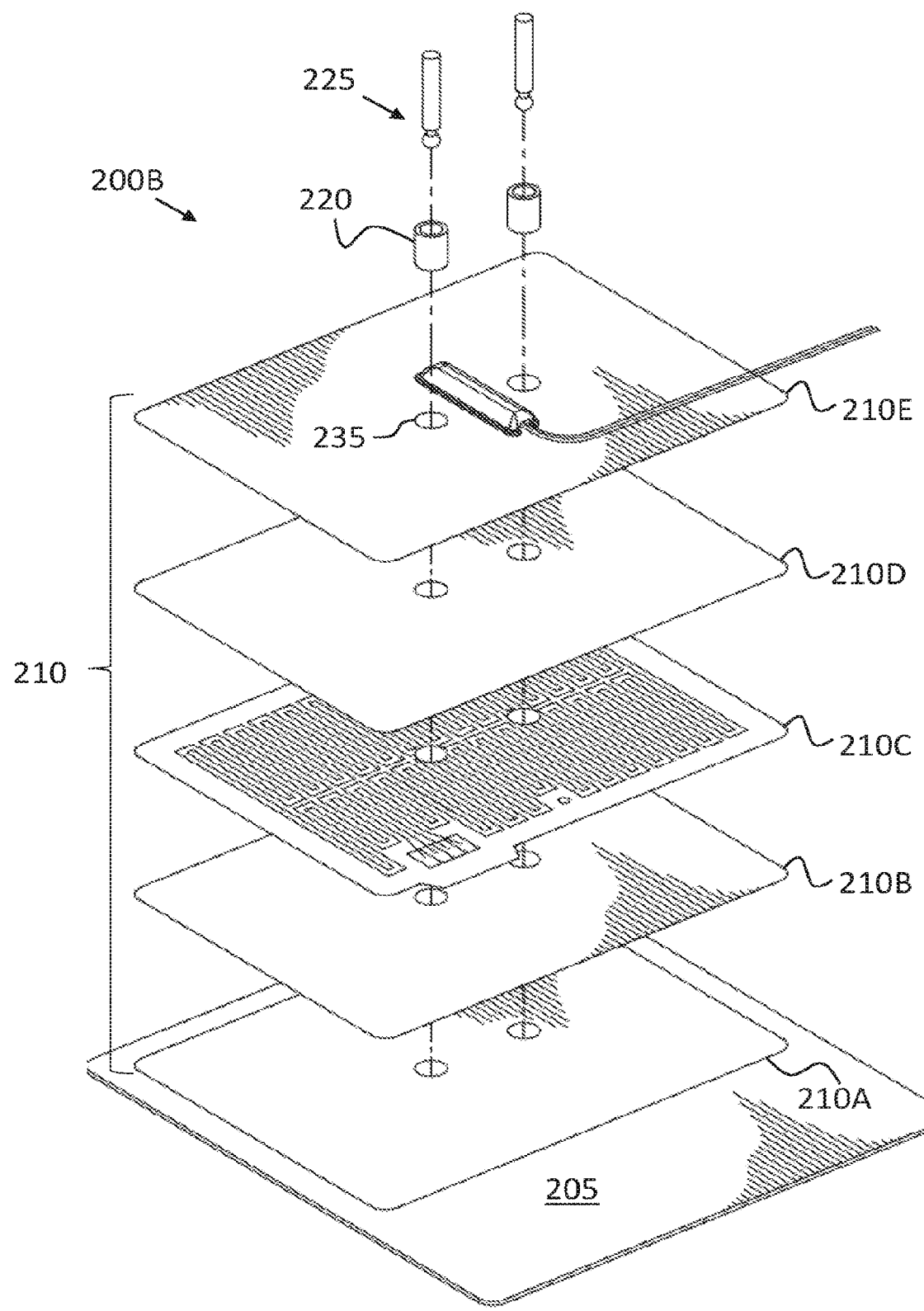
FIG. 2B depicts an exploded view of an exemplary heat source with an exemplary temperature module placed within the heat source.

FIG. 2B depicts an exploded view of an exemplary heat source with an exemplary temperature module placed within the heat source. A heating surface subassembly 200B includes the heat source 210. The heat source 210 includes a bottom layer 210A. The bottom layer 210A is thermally coupled to the heat transfer body 205. The bottom layer 210A is covered by an electrically insulative lower intermediate layer 210B. The lower intermediate layer 210B is thermally coupled to a heating element layer 210C. The heating element layer 210C is covered by an electrically insulative top intermediate layer 210D. The top intermediate layer 210D is thermally coupled to a top layer 210E. In the depicted example, the bottom layer 210A, the lower intermediate layer 210B, the heating element layer 210C, the top intermediate layer 210D and the top layer 210E includes one or more apertures 235. The apertures 235 are substantially aligned when the heat source 210 is assembled. The apertures 235 may allow for insertion of the insulating barrel 220. The barrel 220 may be inserted through the heat source 210 until it is in contact with the heat transfer body 205. Within the insulating barrel 220 is the temperature sensor assembly 225. The fixed location of the insulating barrel 220 may advantageously support repeatable positioning of the temperature sensor assembly 225.

In an illustrative example, the heating surface subassembly 200B may be constructed by first punching one or more apertures (e.g., 235) through a silicone-based heater source (e.g., 210). The apertures may be located in any suitable location. In some examples, at the time the silicone-based heater source is die-cut, the aperture(s) may be punched out in the same process. Next, the silicone-based heater source may be vulcanized to a heat transfer body (e.g., 205). Next, one or more thermal insulating barrels (e.g., 220) may be inserted through the aperture(s). Thermal paste may then be applied into the thermal insulating barrel(s). One or more temperature sensors may then be inserted into the thermal insulating barrel(s). Finally, thermal insulating glue may be applied inside the barrel(s) to fasten the temperature sensor(s) to the thermal insulating barrel(s), and may be applied outside the barrel(s) to fasten the barrel(s) to the silicone-based heater source.

Figure 2C:
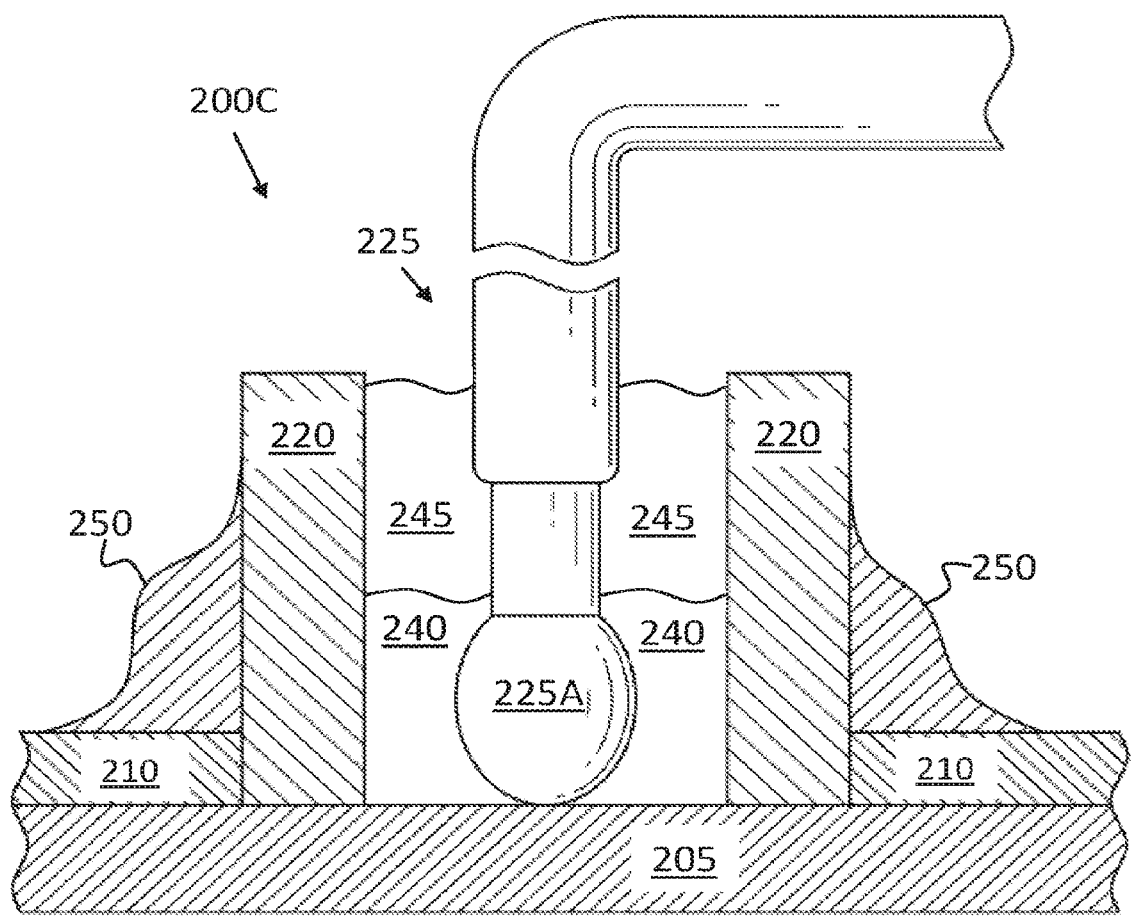
FIG. 2C depicts a cross-sectional view of an exemplary temperature module.

FIG. 2C depicts a cross-sectional view of an exemplary temperature module. A temperature sensor module 200C includes the heat transfer body 205. The heat transfer body 205 is thermally coupled to the heat source 210. The heat source 210 includes an aperture (e.g., FIG. 2B, item 235) which receives the thermal insulating barrel 220. Within the thermal insulating barrel 220 is the temperature sensor assembly 225. The temperature sensor assembly 225 includes a temperature sensing element 225A. The temperature sensing element 225A is thermally coupled to a thermal compound 240. The thermal compound is thermally coupled to the heat transfer body 205.

The thermal compound 240 and the temperature sensor assembly 225 are adhesively coupled to the thermal insulating barrel 220 via an adhesive 245. In some implementations, the adhesive 245 may be potting compound. Accordingly, the temperature sensor assembly 225 may be potted within the thermal insulating barrel 220. An outer surface of the thermal insulating barrel 220 is adhesively coupled to the heat source 210 via an adhesive 250.

In some embodiments, the thermal insulating barrel 220 may mitigate direct thermal interaction with the heat source 210 to the temperature sensing element 225A Further, the temperature sensing element 225A may be in intimate contact directly with the heat transfer body 205, in some implementations. Accordingly, the temperature sensing element 225A may sense and/or measure the temperature of the heat transfer body 205, while maintaining thermal decoupling from the direct heating effects of the heat source 210.

The temperature sensing element 225A may be a temperature sensor. In various examples, the temperature sensor may include one or more thermocouples. Thermocouples may advantageously withstand high temperatures, caustic environments, and may be provided in a small form factor. In some embodiments, the temperature sensor may include one or more metallic resistance temperature detectors (RTDs). Metallic RTDs may advantageously provide high accuracy and repeatability. In some examples, the temperature sensor may include one or more thermistors. Inclusion of a thermistor may advantageously provide substantially rapid response, and high precision over a limited temperature range of about −90° C. to 130° C. The term "substantially rapid" in this example may be defined as less than one second. In some implementations, the temperature sensor may include one or more semiconductor-based temperature sensors. Semiconductor-based temperature sensors may advantageously provide high linearity and high accuracy over an operating range of about −55° C. to 150° C.

In an illustrative example, a warming tray assembly (e.g., FIG. 1A, item 115) on a medical fluid warming device may include the heat transfer body 205. The heat transfer body 205 may warm the blood product. In various examples, the heat transfer body 205 may heat any intravenous fluid. The temperature sensor module 200C may advantageously provide accurate measurements of the temperature of the warming tray assembly, while being thermally decoupled from the direct heating effects of the heat source 210.

FIG. 3 depicts an exploded view of an exemplary heat source with exemplary temperature modules placed outside the perimeter of the heat source. A heating surface subassembly 300 includes a thermal interface substrate 305. The thermal interface substrate 305 is thermally coupled to a heat source 310. A temperature probe 315 is thermally coupled to the thermal interface substrate 305. The heating surface subassembly 300 may include one or more temperature probes 315. In the depicted example, the heat source 310 does not include apertures for the temperature probes 315. The temperature probes 313 are located outside the perimeter of the heat source 310. In the depicted example, a thermally insulating cover 320 is coupled to the temperature probes 315. In some examples, the thermally insulating cover 320 may be placed over the temperature probes 315 and may couple to the thermal interface substrate 305. In various examples, the thermally insulating cover 320 may couple to the thermal interface substrate 305 and the temperature probes 315. In some embodiments, the thermally insulating cover 320 may include various temperature-insulating materials (e.g., ceramic, plastics, rubbers, glass-fiber insulation, spray-on foam-based materials, foam rubber). In some implementations, the thermally insulating cover 320 may include a rigid compartment filled with air or insulation.

In an illustrative example, the thermally insulating cover 320 may substantially insulate the temperature probes 315 from the direct cooling effects of the surrounding air. The temperature probes 315 in a location remote from the heat source 310 may advantageously provide enhanced accuracy measurements of the temperature of the thermal interface substrate 305, while being thermally decoupled from the direct heating effects of the heat source 210.

FIG. 4 depicts an exploded perspective view of an exemplary heater tray in a drop-in form factor. In the depicted example, a heater tray 400 includes a heater tray frame 405. The heater tray frame 405 includes an aperture 410. The perimeter of the aperture 410 includes a recessed step feature 415. The recessed step feature 415 is configured to receive a heater subassembly 420. In an illustrative example, the heater subassembly 420 may fit within the recessed step feature 415. The recessed step feature 415 may be configured to support the heater subassembly 420 such that an upper surface 420A of the heater subassembly 420 is flush with an upper surface 405A of the heater tray frame 405. In some embodiments, the upper surface 420A of the heater subassembly 420 may include alumina. The alumina may advantageously mitigate conduction of electrical current to patients and/or operators who may come in physical contact with the heater subassembly 420.

The heater subassembly 420 includes a power harness 425 and a temperature sensor harness 430. In various examples, the heater subassembly 420 may include one or more temperature sensor harnesses 430. The power harness 425 and the temperature sensor harnesses 430 may be routed on an opposing side of the upper surface 405A of the heater tray frame 405. The design of the heater subassembly 420 may allow a straightforward method for deposition or creation of a chemically formed layer of alumina on one or more surfaces of the heater subassembly 420. The chemically formed layer of alumina may advantageously insulate users, patients and/or operators from electrical leakage currents.

In an illustrative example, the heater tray 400 may be included in a medical fluid warming device which may, for example, provide intravenous therapy to a user. An operator may place a bag of blood product (e.g., FIG. 1, item 110) on the heater tray 400. The heater subassembly 420 may heat the blood product to human body temperature. Accordingly, the heated blood product administered to the user may mitigate user discomfort.

FIG. 5 depicts an exploded perspective view of an exemplary heater tray in a slide-in form factor. In the depicted example, a heater tray 500 includes a heater tray frame 505. The heater tray frame 505 includes a cut-out 510. The perimeter of the cut-out 510 includes a slot 515. The slot 515 is configured to receive a heater subassembly 520. In an illustrative example, the heater subassembly 520 may fit within the slot 515. The slot 515 may be configured to support the heater subassembly 520 such that an upper surface 520A of the heater subassembly 520 is flush an upper surface 505A of the heater tray frame 505.

The heater subassembly 520 includes a power harness 525 and a temperature sensor harness 530. In various examples, the heater subassembly 520 may include one or more temperature sensor harnesses 530. The power harness 525 and the temperature sensor harnesses 530 may be routed on an opposing surface of the upper surface 505A of the heater tray frame 505. Further, the power harness 525 and the temperature sensor harnesses 530 may be enclosed within a device enclosure. The device enclosure may house the electronics and may protect patients and operators from electrical hazards. In addition, the heater subassembly 520 may include an integral insulative chemically formed layer. The device housing, in conjunction with the heater tray 500 may protect patients and operators from electrical hazards within the device housing. This electrical hazard protection may include the heater subassembly 520 with the integral insulative chemically formed layer.

Although various embodiments have been described with reference to the figures, other embodiments are possible. For example, in some implementations, various heat transfer bodies may include a curved shape. Further, various examples of heat transfer bodies may be flat or may be formed in various shapes that may optimize heat transfer to fluids. In some implementations, various temperature sensors may include non-contact measurement, for example, infrared (IR) sensing. The temperature sensors may sense the temperature of a heat transfer body.

In various examples, a thermal interface substrate (e.g., 305) and/or a heating tray (e.g., 400) may include thermally conductive and electrically isolative materials. For example, the thermal interface substrate may be nonmetallic. In some examples, heating elements within the silicon-based layers may be embedded or sandwiched.

In various examples, a thermal interface substrate (e.g., 305) may be metallic. The metallic thermal interface substrate may advantageously provide a cost-effective and thermally conductive interface between a beating element and a liquid to be heated.

The system may be advantageously employed in double-insulated fluid-heating medical applications. For example, the system may be advantageously employed as a blood components heater for blood transfusion devices. In an illustrative example, the system may be advantageously employed in various intravenous (IV) medical applications. In various applications, a patient's body temperature may be maintained. In some examples, various medical devices may remove blood pathogens in patients with AIDS or cancer. In such examples, various fluids may be heated by the system. In addition, a chemically formed layer of alumina on a heat transfer body may mitigate leakage currents to a patient or operator in contact with the heat transfer body. The system may be advantageously employed for other appropriate uses, for example, warming of a dialysate for various dialysis therapies.

In various examples, leakage current measured between a power input harness on a heater assembly and an external surface of a heat transfer body of the heater assembly may be below various regulatory standard thresholds. An alumina substrate on the external surface of the heat transfer body may electrically insulate the heat transfer body from the power input harness. In an illustrative current leakage test case, 85-250 AC $V_{rms}$ may be applied at 50 to 60 Hz between the power input harness and the external surface of the heat transfer body. In such applications, the leakage current is limited to 5 µA or less. Further, the withstand voltage between the power input harness and the external surface of the heat transfer body may be about 2 kV or greater. In some implementations, the withstand voltage between the power harness and the external surface of the heat transfer body may be about 4 kV or greater.

In some embodiments, the chemically formed layer of alumina may be formed, in whole or in substantial part, from an aluminum oxide. The aluminum oxide may include, for example, a chemical makeup of $Al_2O_3$.

In an illustrative example, the heater tray may be included in a medical fluid warming device which may, for example, provide peritoneal dialysis therapy to a user. An operator may place a bag of dialysate on the heater tray. The heater subassembly may heat the dialysate to human body temperature. Accordingly, the heated dialysate administered to the user may mitigate user discomfort.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A heating apparatus, comprising:
   a heat source (210) having a top surface, a bottom surface, and an aperture (235) extending from the top surface, to the bottom surface, wherein the heat source (210) is a silicone heater stack comprising:
      a first silicone-based layer (210A) thermally coupled to a heat transfer body;
      a second silicone-based layer (210B) disposed on top of the first silicone-based layer;
      a heating element layer (210C) disposed on top of the second silicone-based layer;
      a third silicone-based layer (210D) disposed on top of the heating element layer;
      a fourth silicone-based layer (210E) disposed on top of the third silicone-based layer,
   the heat transfer body (205) thermally coupled with the heat source (210) and disposed proximate the bottom surface of the heat source (210), the heat transfer body (205) comprising a thermally conductive material;
   a thermal insulating module (220) extending through the aperture (235) in the heat source (210), the thermal insulating module (220) comprising a cavity extending through the heat source (210);
   a temperature sensor (225) inserted through the cavity of the thermal insulating module (220), the temperature sensor (225) being thermally coupled to the heat transfer body (205) and being thermally decoupled from the heat source (210), such that the temperature sensor (225) is thermally insulated from direct heating effects of the heat source (210); and,
   a thermal breaker (230) thermally coupled to the heat source (210) and configured to shut off power to the heat source (210) when the heat source (210) exceeds a predetermined threshold for a predetermined time.

2. The heating apparatus of claim 1, wherein the thermally conductive material comprises aluminum.

3. The heating apparatus of claim 1, wherein the heat transfer body is at least partially covered with a chemically formed layer of alumina to provide for substantial electrical insulation, such that electrical current leakage from the heat transfer body is reduced.

4. The heating apparatus of claim 1, further comprising a thermal compound (240) disposed in the cavity of the thermal insulating module (220) to facilitate a transfer of heat between the temperature sensor (225) and the heat transfer body (205).

5. The heating apparatus of claim 4, further comprising an adhesive (245) disposed in the cavity of the thermal insulating module (220) for adhesively coupling the temperature sensor (225) to an inner surface of the cavity of the thermal insulating module (220).

6. The heating apparatus of claim 1, wherein the temperature sensor (225) comprises a thermocouple.

7. The heating apparatus of claim 1, wherein the temperature sensor (225) comprises a thermistor.

8. The heating apparatus of claim 1, wherein the heat transfer body (205) is a planar shape.

9. The heating apparatus of claim 1, wherein the heat source (210) is a planar shape.

10. A heating apparatus, comprising:
a heat source (210) having a top surface, a bottom surface, and an aperture (235) extending from the top surface (210E) to the bottom surface, wherein the heat source (210) is a silicone heater stack comprising:
  a first silicone-based layer (210A) thermally coupled to a heat transfer body;
  a second silicone-based layer (210B) disposed on top of the first silicone-based layer;
  a heating element layer (210C) disposed on top of the second silicone-based layer;
  a third silicone-based layer (210D) disposed on top of the heating element layer;
  a fourth silicone-based layer (210E) disposed on top of the third silicone-based layer,
the heat transfer body (205) thermally coupled with the heat source (210) proximate the bottom surface of the heat source (210), the heat transfer body (205) comprising a thermally conductive material
a thermal insulating module (220) extending through the aperture (235) in the heat source (210), the thermal insulating module (220) comprising a cavity extending through the heat source (210); and,
a temperature sensor (225) inserted through the cavity of the thermal insulating module (220), the temperature sensor (225) being thermally coupled to the heat transfer body (205) and being thermally decoupled from the heat source (210) such that the temperature sensor (225) is thermally insulated from direct heating effects of the heat source (210).

11. The heating apparatus of claim 10, wherein the thermally conductive material comprises aluminum.

12. The heating apparatus of claim 10, wherein the heat transfer body is at least partially covered with a chemically formed layer of alumina to provide for substantial electrical insulation, such that electrical current leakage from the heat transfer body is reduced.

13. The heating apparatus of claim 10, further comprising a thermal compound (240) disposed in the cavity of the thermal insulating module (220) to facilitate a transfer of heat between the temperature sensor (225) and the heat transfer body (205).

14. The heating apparatus of claim 13, further comprising an adhesive (245) disposed in the cavity of the thermal insulating module (220) for adhesively coupling the temperature sensor (225) to an inner surface of the cavity of the thermal insulating module (220).

* * * * *